Dec. 26, 1972 G. H. MACK ET AL Plant Pat. 3,277
CHRYSANTHEMUM PLANT
Filed March 30, 1971
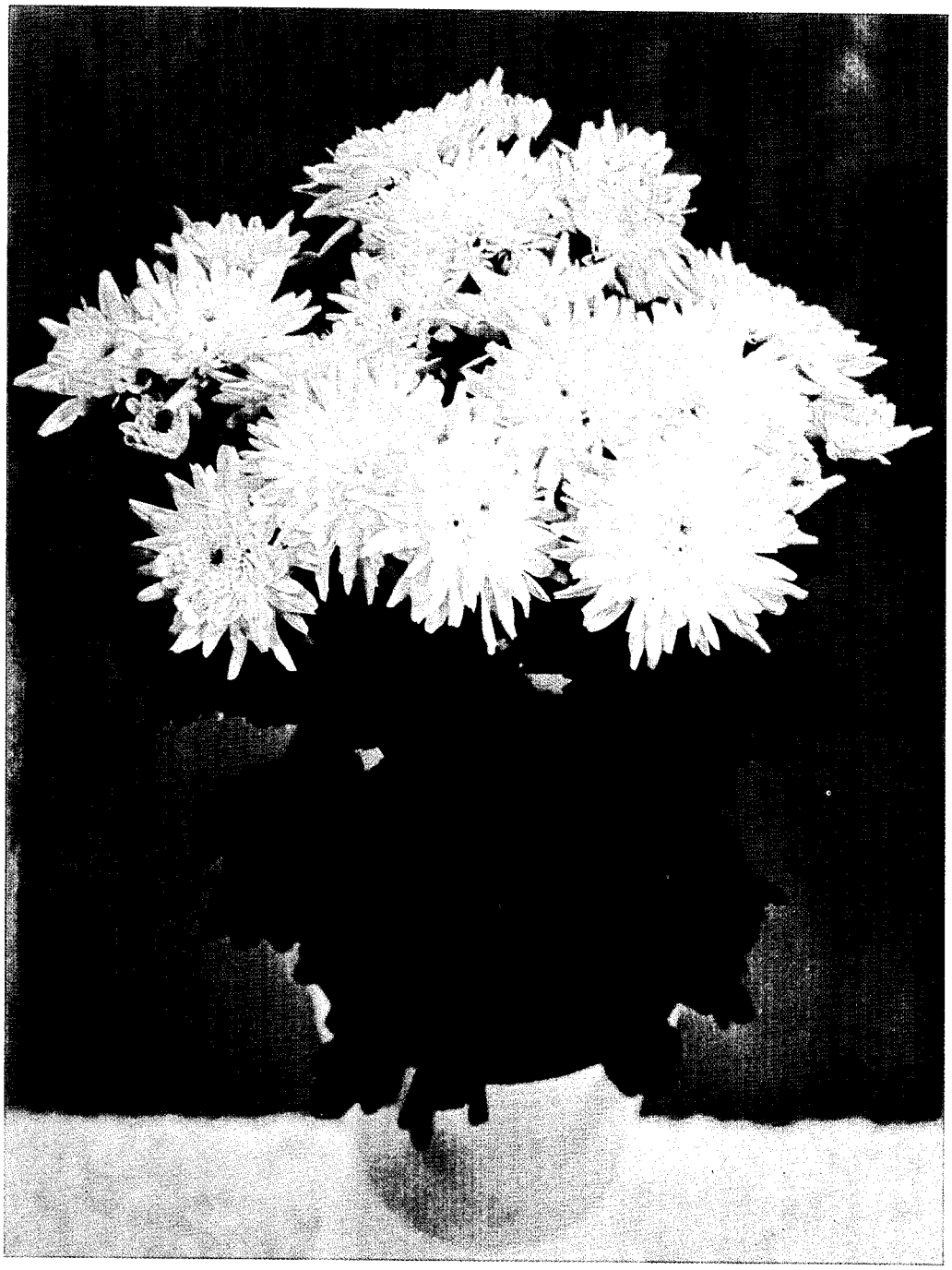

United States Patent Office

Plant Pat. 3,277

Patented Dec. 26, 1972

3,277
CHRYSANTHEMUM PLANT

Grace H. Mack, New Canaan, Conn., and Walter H. Jessel, Jr., Doylestown, and William E. Duffett, Akron, Ohio, assignors to Grace H. Mack, New Canaan, Conn.

Filed Mar. 30, 1971, Ser. No. 129,646

Int. Cl. A01h *5/00*

U.S. Cl. Plt.—75 1 Claim

The present invention comprises a new and distinct cultivar of chrysanthemum plant of the garden variety type which is a seedling of parents identified as #MX501–63×#617–66. Both parents are unpatented and identified by the above numbers to distinguish the parents from others in the same breeding program.

The new cultivar is characterized particularly by its early response and its compact cushion habit and is similar in these respects to the cultivar Early Gold, an unpatented cultivar sold commercially by Yoder Brothers, Inc., the assignee of the present invention. In varieties having these characteristics, there are relatively few which are generally yellow in color, and the new cultivar fills a definite need in the general grouping indicated.

The new cultivar is also similar to Early Gold in its flowering period but is distinguished from Early Gold by the following characteristics:

(1) Flowers ¾″ larger.
(2) Stronger stems.
(3) More decorative flower form.
(4) Ten days longer keeping quality under outdoor garden conditions.
(5) Lighter yellow color.
(6) Taller, more spreading, more prolific habit.
(7) Lighter colored and larger foliage.
(8) More prominent stipules.
(9) Less serration to the leaf.

The new cultivar was selected from the progeny of the designated cross and when asexually reproduced by cuttings at Barberton, Ohio, has been found to retain its distinctive characteristics through successive propagations.

The new cultivar when grown in the vicinity of Barberton, Ohio, has a response period of approximately 7 weeks, and a natural flowering date of approximately October 1. The following detailed description is based on observations made of the new cultivar both in a greenhouse and outdoors in Barberton, Ohio. The response time, blooming period, color, and total vigor may vary significantly with varying environmental conditions such as temperature, day length, and light intensity. Suggested flowering in the northern and western United States and coastal California is from mid-April through May and mid-September through mid-October.

The accompanying drawing shows the unique characteristics of the new cultivar, the color being as nearly true as possible with color illustrations of this type.

In the following description, color references are to the Munsell Color Book, 1963 edition, and comparisons made with the cultivar Early Gold. Where only a single value or description is listed, such value or description applies also to the comparison cultivar.

Botanical Classification: *Chrysanthemum morifolium*

| | Jackpot | Early Gold |
|---|---|---|
| Bloom: | | |
| Size | 2″ | 1¼″. |
| Fully expanded | 2¾″ | 1⅝″. |
| Borne | Clusters on elongated pedicels | Clusters on elongated pedicels. |
| Stems | Strong | Moderately strong. |
| Form | Decorative | Intermediate pompon. |
| Permanence | 20 days | 10 days. |
| Color: | | |
| Center of flower | Yellow, 7.5Y8.5/12 | Dark yellow, 5Y8.5/12. |
| Base of petals | Yellow, 7.5Y8.5/10 | Do. |
| Inside of petals | do | Do. |
| Reverse of petals | Yellow, 7.5Y8.5/8 | Yellow, 5Y8.5/10. |
| Tonality from a distance | Yellow | Yellow. |
| Discoloration | Yellow, 7.5Y8.5/8 | Yellow, 5Y8.5/8. |
| Petals: | | |
| Texture | Smooth | Smooth. |
| Appearance and form | Open at base, broad flat petal, numerous ridges, tapering to a blunt point. | Open at base, broad shallow keel, tapering to a blunt point. |
| Arrangement | Composite, whorled on a single receptacle | Composite, whorled on a single receptacle. |
| Persistence | Resists shatter | Resists shatter. |
| Fragrance | Typical chrysanthemum | |
| Reproductive organs: | | |
| Stamen, anthers | None | 4–5. |
| Pollen | None | |
| Arrangement | Clustered in center of flower, if present | |
| Styles | Present ray florets | |
| Length | Short | |
| Ovaries | At the base of petal attached to receptacle | |
| Plant: | | |
| Form | Herbaceous | |
| Growth | Compact—spreading | |
| Height | Approximately 9″ when flowered naturally as field grown plants from a planting made in mid-June and given a single pinch in late June. | Approximately 8″ when flowered naturally as field grown plants from a planting made in mid-June and given a single pinch in late June. |
| Spread (Fall garden) | Approximately 21″ when flowered naturally as field grown plants from a planting made in mid-June and given a single pinch in late June. | Approximately 14″ when flowered naturally as field grown plants from a planting made in mid-June and given a single pinch in late June. |
| Foliage: | | |
| Top side | Dark green, 5GY3/4 | Dark green, 7.5GY3/4. |
| Size | 3″ long, 2¼″ wide | 2½″ long, 1½″ wide. |
| Quantity | Numerous | |
| Shape | Spatulate lobed | |
| Texture | Smooth | |
| Ribs and veins | Prominent | |
| Edge | Moderately indented | |
| Serration | Slight | Moderate. |
| Underside | Light green, 7.5GY5/4 | Light green, 7.5GY5/4. |
| Stipules | Rudimentary to prominent | Rudimentary. |

We claim:

1. A new and distinct cultivar of chrysanthemum characterized particularly as to its uniqueness when compared to the cultivar Early Gold by its ¾″ larger flowers, stronger stems, more decorative flower form, 10 days longer keeping quality, lighter yellow color, taller, more spreading, more prolific habit, lighter colored and larger foliage, more prominent stipules, and less leaf serration.

No references cited.

ROBERT E. BAGWILL, Primary Examiner